(12) United States Patent
Ryan et al.

(10) Patent No.: US 9,621,602 B2
(45) Date of Patent: Apr. 11, 2017

(54) IDENTIFYING AND PROVIDING PHYSICAL SOCIAL ACTIONS TO A SOCIAL NETWORKING SYSTEM

(71) Applicant: Facebook, Inc., Menlo Park, CA (US)

(72) Inventors: Timothy Cameron Ryan, Medford, MA (US); Jialiya Huang, Needham, MA (US); Paul Henry Booth, Needham, MA (US); Jonathan Andrew McKay, San Diego, CA (US); Seungwhan Moon, Needham, MA (US); Margaret-Ann Julia Seger, Needham, MA (US); Amon Daran Millner, Cambridge, MA (US); Peter Xiu Deng, Los Altos Hills, CA (US); Christopher John Marra, San Francisco, CA (US); Scott Andrew Thomson, San Francisco, CA (US); Gregory Matthew Marra, San Francisco, CA (US)

(73) Assignee: Facebook, Inc., Menlo Park, CA (US)

( * ) Notice: Subject to any disclaimer, the term of this patent is extended or adjusted under 35 U.S.C. 154(b) by 181 days.

(21) Appl. No.: 14/090,252

(22) Filed: Nov. 26, 2013

(65) Prior Publication Data
US 2014/0149514 A1 May 29, 2014

Related U.S. Application Data

(60) Provisional application No. 61/730,386, filed on Nov. 27, 2012.

(51) Int. Cl.
*H04L 29/06* (2006.01)
*H04W 4/20* (2009.01)
*G06Q 50/00* (2012.01)
*H04L 29/08* (2006.01)
(Continued)

(52) U.S. Cl.
CPC ............ *H04L 65/403* (2013.01); *H04L 67/12* (2013.01); *H04L 67/22* (2013.01); *H04L 67/26* (2013.01); *H04W 4/206* (2013.01); *G06Q 50/01* (2013.01); *H04L 67/30* (2013.01); *H04W 4/008* (2013.01); *H04W 4/02* (2013.01); *H04W 4/027* (2013.01)

(58) Field of Classification Search
None
See application file for complete search history.

(56) References Cited

U.S. PATENT DOCUMENTS

2008/0208925 A1* 8/2008 Shum .................... H04W 12/06
2010/0261526 A1* 10/2010 Anderson ............... G06F 3/017
463/31

(Continued)

*Primary Examiner* — Ninos Donabed
(74) *Attorney, Agent, or Firm* — Fenwick & West LLP

(57) ABSTRACT

Physical social actions are conveniently detected, characterized, and provided to a social networking system. This improves the user experience of the social networking system by more thoroughly recording the social actions of users occurring outside a social graph. This has the effect of extending an open social graph, which typically refers to social actions taken outside the social networking system but within a computer network, to physical social actions. By providing characterized physical social actions to the social networking system, the open social graph is extended to include physical social actions.

28 Claims, 3 Drawing Sheets

(51) Int. Cl.
*H04W 4/00* (2009.01)
*H04W 4/02* (2009.01)

(56) References Cited

U.S. PATENT DOCUMENTS

| | | | | |
|---|---|---|---|---|
| 2011/0126102 | A1* | 5/2011 | Archer | H04N 21/4147 715/716 |
| 2011/0264736 | A1* | 10/2011 | Zuckerberg | G06Q 30/02 709/204 |
| 2012/0117020 | A1* | 5/2012 | Davis | G06F 19/345 706/54 |
| 2012/0151322 | A1* | 6/2012 | Lindsay | G06Q 50/01 715/234 |
| 2012/0278166 | A1* | 11/2012 | Badros | G06Q 50/01 705/14.53 |
| 2012/0290950 | A1* | 11/2012 | Rapaport | H04L 51/32 715/753 |
| 2013/0095924 | A1* | 4/2013 | Geisner | A63F 13/00 463/32 |
| 2013/0110666 | A1* | 5/2013 | Aubrey | G06Q 30/0269 705/26.5 |
| 2013/0151515 | A1* | 6/2013 | Davis | G06Q 50/01 707/736 |
| 2013/0238544 | A1* | 9/2013 | Kunjithapatham | G06F 17/30867 706/47 |
| 2013/0311411 | A1* | 11/2013 | Senanayake | G06F 3/013 706/13 |

* cited by examiner

IDENTIFYING AND PROVIDING PHYSICAL SOCIAL ACTIONS TO A SOCIAL NETWORKING SYSTEM

CROSS REFERENCE TO RELATED APPLICATIONS

This application claims the benefit of U.S. Provisional Application No. 61/730,386, filed Nov. 27, 2012, which is incorporated by reference in its entirety.

BACKGROUND

Embodiments described herein relate generally to providing information to a social networking system. Specifically, embodiments described herein relate to identifying and providing physical social actions to a social networking system.

Social networks, or social utilities that track and enable connections between users (including people, businesses, and other entities), have become prevalent. In particular, a social networking system allows users to more efficiently communicate information that is relevant to their friends or other connections in the social network. Social networks typically incorporate a system for maintaining connections among users in the social network and links to content that are likely to be relevant to the users. Social networks also collect and maintain information about the users of the social network. This information may be static, such as geographic location, employer, job type, age, music preferences, interests, and a variety of other attributes, or it may be dynamic, such as tracking a user's actions within the social network.

Additionally, a social networking system may receive information describing the interactions of its users with entities external to the social networking system. For example, social networking system users may purchase goods or services from vendors at physical retail locations or through websites associated with the vendors. The social networking system users may then elect to share this information with the social networking system. Incorporating this external information provides the social networking system with additional information about its users, thereby allowing the social networking system to provide a wider range of information to its users. Because social networking system users are likely to have diverse interests and demographic characteristics, adding information about activities occurring external to the social networking system allows further analysis of social networking system users.

While incorporating a user's interactions external to the social networking system enriches the social networking system experience, users typically perform innumerable social actions every day that are not added to the system. In some cases, the social actions are not added because, even though informative, they escape the notice of the user. In other cases, the social actions are not added to the social networking system because it is not convenient for the user to do so. In particular, physical social actions performed without the aid of a computing device or intentional use of the social networking system may be less convenient to contribute to the social networking system. This is particularly true during times when a user engages in many brief social interactions, such as meeting people at a party or a conference. Regardless of the reason, the social networking experience could be enriched by providing the social networking system with descriptions of physical social interactions.

SUMMARY

A system is described for extending an open social graph, which typically refers to social actions taken outside the social networking system but within a network, to physical social actions. This is accomplished using a system that can detect physical movement of a user, compare the movement to a baseline movement profile that is associated with a physical social action, and characterize the detected physical movement accordingly. The characterized physical social action is then posted to the social networking system account of the user

The figures depict various embodiments of the present disclosure for purposes of illustration only. One skilled in the art will readily recognize from the following discussion that alternative embodiments of the structures and methods illustrated herein may be employed without departing from the principles of the embodiments described herein.

DETAILED DESCRIPTION

Overview

The described embodiments enable physical social actions to be conveniently detected, characterized, and provided to a social networking system. By conveniently providing physical social actions to the social networking system, the user experience of the social networking system is improved by more thoroughly recording the social actions of users occurring outside a social graph that typically includes actions occurring within a social networking system or within external websites and/or mobile applications in communication with the social networking system and not actions occurring physically. This has the effect of extending an open social graph, which typically refers to social actions taken outside the social networking system but within a network, to physical social actions. In other words, by providing characterized physical social actions to the social networking system, the open social graph may be seamlessly extended to include physical social actions. Identified social actions, once communicated to, or determined by, a social networking system are used to identify prospective connections between users not currently connected, post updates related to a user so that other connected users are apprised of the user's status, or otherwise communicate information to connected users.

System Environment for Identifying and Characterizing Physical Social Actions

Figure 1:
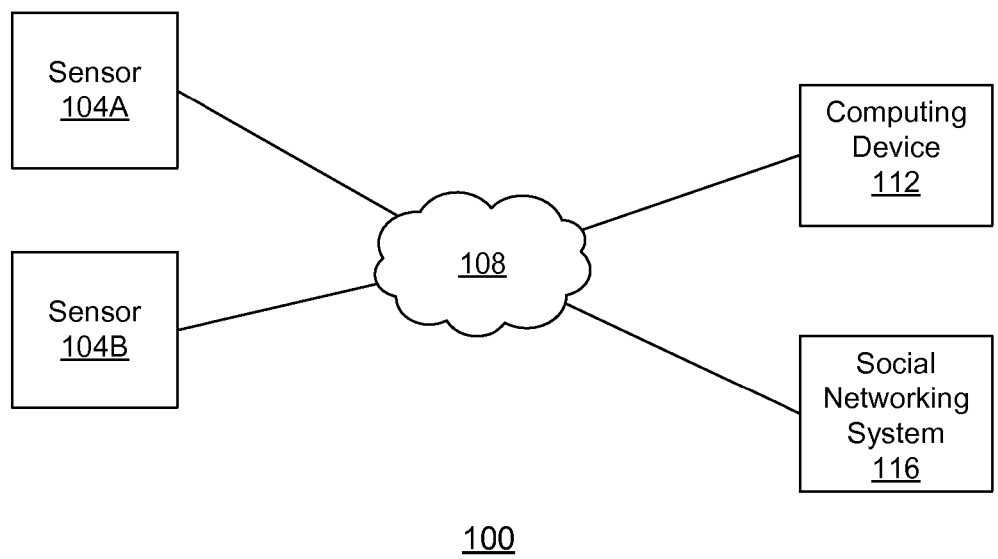
FIG. 1 is a system environment in which a physical interaction system identifies, characterizes, and provides physical social actions to a social networking system, in an embodiment.

FIG. 1 illustrates one example of a system environment 100 in which a physical interaction system detects a movement of a user and/or proximity of another user (whether a human user, or a non-human user, such as an animal or an inanimate object), collects data corresponding to the movement and/or proximity, and characterizes the data as corresponding to a physical social action. The characterization of a user's movement as a physical social action enables the open social graph to be conveniently extended to physical social actions without requiring the user to expressly record the social action in the social networking system 116. The interactions between the various elements of FIG. 1 are discussed in more detail in the context of FIG. 3. The system environment 100 of FIG. 1 includes sensors 104A and 104B (referred to collectively and/or generally as "104"), a network 108, a computing device 112, and a social networking system 116.

The sensor 104 of the system environment 100 is used to detect physical movement of a user of the social networking system 116 that corresponds to one or more social actions. The sensor may be located on the user, on an item carried by the user, or otherwise associated with the user. In some embodiments, the sensor 104 records a data profile characterizing the detected movement. Note that the terms "data profile," "movement profile," and "physical movement profile" are used in this specification to refer to the "data profile characterizing the detected movement." The data comprising the data profile is a function of the movement, the type of sensor 104 and the type of movement that the sensor is configured to detect. In one example, the data profile includes one or more data points of acceleration as a function of time for a sensor 104 that includes an accelerometer. In another example, the data profile includes one or more data points of geographic location coordinate as a function of time for a sensor 104 that includes a global positioning system (GPS) sensor. In yet another example, the data profile includes one or more data points of orientation in three-dimensions for a sensor 104 that include a gyroscope. In still other examples, the sensor 104 and the corresponding data profile includes another type of movement and/or location sensor, or a combination of more than one type of sensor.

The sensor 104 also detects other physically proximate sensors 104, whether associated with a human user or a non-human user to which a sensor is attached (e.g., a door handle, a door, a kiosk, an establishment, a collar of an animal, an animal, a book, a bicycle, a vehicle, a mobile computing device, an article of clothing, a workstation or desk). By identifying other proximate sensors 104 and communicating the corresponding sensor identities along with a data profile of a user movement, a user movement may be characterized as a physical social action by the system 100, as described below. An embodiment of a sensor 104 will be described in detail in the context of FIG. 2A.

The sensor 104 may be configured to fit within a mobile computing device, a wrist watch, or other personal accessory worn by (or otherwise carried by) the user. In one embodiment, the sensor 104 may be used to detect movements of a portion of a user, such as an arm or leg, on which the sensor is disposed. For example, if the sensor 104 is disposed on (or in) a wrist-watch or wrist-band worn on an arm of the user, the sensor may be used to detect movements of the arm or movements of the user that cause the arm to move. Such movements include opening a door, shaking hands, waving, walking, and others. The location of the user at which the sensor is worn or carried can also be provided with a data profile stored in a processor of the sensor or stored in a user profile of the social networking system for use in the characterization of a data profile as a physical social action.

The sensor 104 can be paired with a user account on, for example, a computing device 112 and/or a social networking system 116 by executing a recognized pairing movement while logged into the user account. Examples of recognized pairing movements include shaking the sensor 104 while simultaneously tapping a key on a keyboard of a computing device logged into a social networking system 116 or simultaneously shaking a mobile computing device having an accelerometer while being logged into the social networking system.

While a specific example of the sensor 104 that includes an RFID transceiver and, optionally, an accelerometer is presented below, the sensor is not limited to this particular example. The sensor 104 can also include image capture systems (such as digital cameras, video recorders, webcams, etc.) that can be used to identify a proximate user and/or inanimate objects, and any related physical social interaction. The sensor 104 may also include audio capture systems that can be used to identify a proximate user and/or inanimate object, and any associated physical social interactions.

As mentioned above, the sensor 104 can be attached to, or integrated with, an inanimate object to identify physical social actions between inanimate objects or between a human user and an object. Examples of inanimate objects include, but are not limited to, a door handle, a door, a kiosk, an establishment, a collar of an animal, a book, a bicycle, a vehicle, a mobile computing device, an article of clothing, and a workstation or desk. In some examples, the physical social actions are defined, in part, based on the inanimate object to which the sensor 104 is attached. For example, if the sensor 104 is attached to a book, the social physical actions that can be performed on the book include, but are not limited to, handling or buying the book, throwing the book, presenting the book to another person, turning a page, reading some or all of the book, and checking the book out from a library. Examples of actions between an inanimate object and a user are described below. The sensors can be ones placed on the objects by the user or can be already existing sensors on the objects (e.g., in an existing pet locator chip inside a pet).

Using the network 108, the sensor 104 provides an identity of the user and the data profile of a movement to the computing device 112 for characterization of the movement as a physical social action. The network 108 may comprise any combination of local area and/or wide area networks, using both wired and wireless communication systems. In one embodiment, the network 108 uses standard communications technologies and/or protocols. Thus, the network 108 may include links using technologies such as Ethernet, 802.11, worldwide interoperability for microwave access (WiMAX), 3G, 4G, CDMA, digital subscriber line (DSL), etc. Similarly, the networking protocols used on the network 108 may include multiprotocol label switching (MPLS), transmission control protocol/Internet protocol (TCP/IP), User Datagram Protocol (UDP), hypertext transport protocol (HTTP), simple mail transfer protocol (SMTP) and file transfer protocol (FTP). Data exchanged over the network 108 may be represented using technologies and/or formats including hypertext markup language (HTML) or extensible markup language (XML). In addition, all or some of links may be encrypted using conventional encryption technologies such as secure sockets layer (SSL), transport layer security (TLS), and Internet Protocol security (IPsec).

Upon receiving an identity of the sensor 104 (associated in some examples with a social networking system user identity) and a data profile of a user's movement, the computing device 112 analyzes the received data profile. This analysis is used to characterize the data profile as corresponding to a physical social action. In one example, the computing device 112 stores baseline data profiles used as references for analyzing a data profile as a specific physical social action. For example, a baseline data profile having a waveform that includes a cyclic displacement of between 2 cm and 5 cm and a frequency of between 1 Hz and 3 Hz may be associated with handshaking. In another example, a baseline data profile that includes a rotation in orientation of between 60° and 120° can be used to characterize a movement as turning a door handle that opens a door. Using similarly characterized baselines, the computing device 112 compares the received data profile to the stored baseline data to characterize the received data profile as a physical social action.

A baseline data profile may also be created by using one or more machine learning algorithms that use sensor 104 data from a plurality of proximate sensors to identify baselines. In effect, machine learning and crowd-sourcing are used in combination to create baseline profiles that can then be used to identify a physical social action corresponding to a received data profile. Machine learning techniques and algorithms include, but are not limited to, neural networks, naïve bayes, and support vector machines.

In another example, multiple data profiles from multiple, physically proximate, sensors (e.g., sensors 104A and 104B) may be received and analyzed contemporaneously to facilitate characterization of a physical social action involving the multiple sensors. For example, if the computing device 112 receives two user identities and two data profiles from sensors 104A and 104B corresponding to contemporaneous movement that matches a baseline profile for handshaking, and optionally receives from the sensors an indication that sensor 104A and 104B are physically proximate, the computing device may infer that the users of sensors 104A and 104B have shaken hands. Other examples can include a sensor 104 associated with a non-human, such as a door handle that, when moved, is associated with the physical social action of entering an establishment. To improve the reliability of this analysis of the system 100, more advanced signal correlation algorithms can be used to validate the received data profiles as actually contemporaneous. Examples of these algorithms include cross correlation.

The computing device 112, having characterized a physical social action between one or more identified users of sensors 104A and 104B, may transmit the characterized physical social action through the network 108 to the social networking system 116. Using an application programming interface ("API") of the social networking system 116, the computing device posts the physical social action to the social networking system account(s) of the identified user(s), thereby extending the open social graph to physical interactions. Continuing with the preceding example, the handshake between the users of sensors 104A and 104B that is published to the social networking system can include "user A met user B" or "user A shook hands with user B."

In a still further example, the two users need not both be human. If the sensor 104B is connected to a door of an establishment, and the sensor 104A communicates a data profile matching a baseline profile of opening a door and is proximate to sensor 104B, then the social networking system 116 can indicate that "user A visited establishment B."

Example Sensor

Figure 2A:
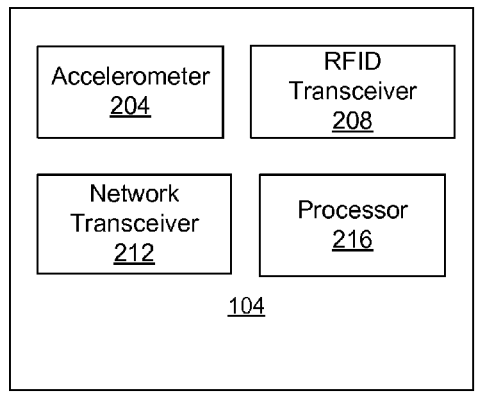
FIG. 2A is a block diagram of a sensor used to detect physical social actions and other physically proximate sensors, collect a data profile of a movement, and provide the data profile of the movement to a computing device for characterization, in an embodiment.

FIG. 2A is a block diagram of an embodiment of a sensor 104 used to detect movements of users and other physically proximate sensors, collect a data profile of a movement, and transmit the data profile (and an associated sensor 104 identity) to a computing device for characterization. In the embodiment shown, the sensor 104 includes an accelerometer 204, a local area identity transceiver 208, a network transceiver 212, and a processor 216. As explained above, the sensor 104 can include any type of movement, location, or orientation sensor, and/or combinations thereof (generically termed "sensors"). The accelerometer 204 is described in this example only for convenience.

In one example, the accelerometer 204 may include one or more accelerometers to detect changes in speed, direction, and/or orientation of the user, thereby indicating user movement. The one or more accelerometers may include a single-axis accelerometer, a multi-axis accelerometer, or combinations thereof. The one or more accelerometers may be micro-machined, such as those used in mobile computing devices, or any other type of accelerometer that is capable of detecting a change in speed, direction, and/or orientation of some or all of a user.

The local area identity transceiver 208 is encoded with a unique identifier that can correspond to the identity of the user of the sensor 104. For example, the local area identity transceiver may be encoded in non-volatile memory with a unique identifier that the user then links with the user's social networking system 116 account. In some examples, this identifier is the user's social security number, a user ID and password, a mobile phone number, or other unique identifier. Regardless, the local area identity transceiver 208 is used to identify the sensor 104 to other proximate sensors, and to identify the user to the social networking system 116. In some examples, the local area identity transceiver 208 can use any of a variety of local communication devices and corresponding transmission protocols. In the example described below, a radio frequency identity (RFID) transceiver will be used for convenience of description.

In another embodiment, the RFID transceiver 208 wirelessly detects other physically proximate sensors 104 and communicates these identities to the social networking system 116. The presence of proximate sensors 104 informs the characterization of a movement profile as a possible physical social action. As described above, examples of contemporaneous movements from proximate devices can be characterized as "user A met user B" or "user A visited establishment B." In some examples, an RFID transceiver 208 identifies all proximate sensors 104, whether the proximate sensors are participating in a contemporaneous movement or not. By identifying proximate sensors and communicating their identities to the computing device 112, the computing device can limit the physical social actions to those users that are proximate to one another. This information can also be used to limit the types of possible physical social interactions used to characterize the movement. For example, a coordinated movement between a door and a human user is limited to the human user opening, closing, and/or bumping into the door.

Furthermore, using the transmitted identities of proximate sensors 104, the computing device 112 can record the interactions experienced by each user over a period of time. This can aid a user in remembering and optionally manually characterizing, the social interactions that have occurred that involve the user. This function is particularly helpful for settings in which many brief social encounters occur, such as at conferences and parties. This feature can also be helpful for remembering unanticipated physical social actions, such as a chance encounter between acquaintances.

In some examples of the sensor 104, the accelerometer 204 (or other type of sensor) is not included, and the data profiles sent to the computing device 112 transmit the identities of proximate sensors. In some embodiments of these examples, the sensor 104 can still be used to detect movement using the RFID transceiver 208. That is, by detecting other proximate sensors 104, and the identities of the proximate sensors, the movements of a user can be inferred. For example, if a sensor 104A becomes proximate to a first sensor 104B, then leaves the first sensor to become proximate to a second sensor 104C, wherein sensors 104B and 104C are attached to stationary objects (e.g., buildings), then the system 100 can infer that the sensor 104A is moving.

The network transceiver 212 is used to wirelessly transmit data from the sensor 104 through the network 108 to the computing device 112. The data transmitted to the computing device 112 may include a data profile of a movement, an identifier of a sensor 104 (e.g. 104A), an identifier of physically proximate sensor 104 (e.g., 104B), and combinations thereof. In one example, the network transceiver 212 transmits the data from the sensor 104 to the computing device 112 using wireless radio frequency transmission protocols based on IEEE 802.11 standards, such as WLAN. In other examples, the network transceiver 212 transmits the data to the network using any wireless data transmission technology including, but not limited to, WiMAX, 3G, 4G, and/or CDMA.

In still further examples the network transceiver 212 may use combinations of wireless technologies and/or wirelessly enabled communication devices to communicate data through the network 108 to the social networking system 116. In one embodiment, the network transceiver 212 of the sensor 104 may be configured to communicate to a mobile computing device using a wireless transmission protocol based on the IEEE 802.11 standard. The mobile computing device connects to the social networking system 116 via the network 108 using, for example a 3G, 4G, and/or CDMA communication network. This then bridges the connection between the network transceiver 212 and the network 108 to communicate a data profile to the social networking system 116.

The processor 216 may be configured to receive and store data from the accelerometer 204, timestamp the data received from the accelerometer, record an identity of a proximate sensor 104 received by the RFID transceiver, communicate stored data to the network transceiver 212, and/or provide operating instructions to some or all of the elements of the sensor. The processor 216 may include some or all of a memory unit, an input/output bus, and various logic elements for execution of computer executable code.

In some embodiments, the processor 216 may assume some or all of the functions of the computing device 112. That is, the processor 216 may store baseline data profiles of movements that are particular to a user or generic to some or all users of the social networking system 116. The processor 216 may also characterize the data profile of a movement as a physical social action by comparing the data profile of the movement to the stored baseline profile. This characterization may then be communicated to the social networking system 116 as a physical social action. Alternatively, the social networking system 116 can assume some or all of the functionality of the computing device 112. Further, the functionality attributed to various entities and modules herein may be distributed between entities and elements in a different manner.

Similarly, the processor 216, through the RFID transceiver 208, may control communications with physically proximate sensors 104, which can include exchanging identities and/or data profiles of detected movements with other proximate sensors. By exchanging data profiles in this way, the processor 216 can analyze data profiles of physical actions occurring contemporaneously. This information can be used to limit the possible physical social actions used to characterize a received data profile to certain types of physical social actions or to certain users, as described above. Also, when used in conjunction with the stored baseline profiles, identifying the relative timing of multiple received data profiles may contribute to the characterization of the movement as a physical social action. That is, understanding that certain actions (such as shaking hands) occur contemporaneously and between two users at a time can inform the characterization of a received data profile.

Although not shown in FIG. 2A, some examples of the sensor 104 also include a device for identifying the location of the sensor (and presumably the location of a user associated with the sensor). Embodiments of such a location detection device include a global positioning system transceiver or other location transceiver that use one or more networks 108 to identify the location of the user. Location information generated by such a device may be transmitted to the computing device 112 for use as part of the characterization of one or more data profiles as a physical social action.

Figure 2B:
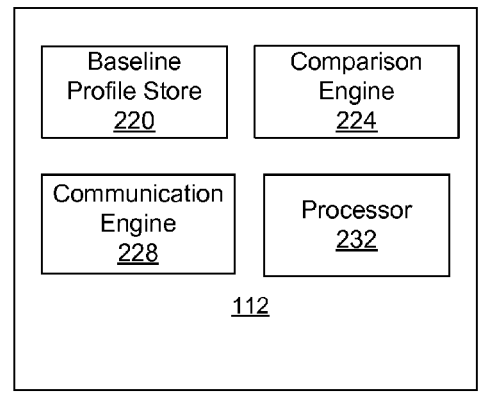
FIG. 2B is a block diagram of a computing device used to receive one or more data profiles of movements, characterize a profile as a physical social action, and post the characterized action to a social networking system, in an embodiment.

FIG. 2B illustrates an example of the computing device 112, which includes a baseline profile store 220, a comparison engine 224, a communication engine 228, and a processor 232. While the computing device 112 is depicted separately in this example for convenience of description, the functions performed by the computing device 112 can be incorporated into any of the other elements of the system environment 100. For example, the functions of the computing device 112 could be incorporated directly into the social networking system 116, the sensor 104, a mobile communications device (not shown), another computing device or computing system, or combinations thereof.

The baseline profile store 220 stores data profiles that have been previously identified as corresponding to specific physical social actions. In some embodiments, these baseline profiles are generic to all users. In other embodiments, the baseline profiles are specific to specific users and are therefore associated with unique user identifiers. In this latter case, because the baseline data profiles are associated with a specific user, the baseline data profiles may be different between users while still identifying the same social action.

For example, a user may indicate to the computing device 112 that a baseline profile for a physical social action, such as shaking hands, will be provided to the baseline profile store 220. This profile may then be provided as a baseline by the user by actually shaking hands and labeling the profile (in this case having a sinusoidal waveform that describes the acceleration of a shaken hand) as such in the baseline profile store 220. In other examples, the user, using the sensor 104, transmits a data profile of a physical social action to the computing device 112, and subsequently identifies the profiles as a baseline profile corresponding to specific physical social actions.

Furthermore, while many of the examples presented herein describe the interaction of two motion sensors 104 for convenience, the interactions and characterizations need not be limited to two devices. Rather, interactions can be defined or inferred between multiple devices. For example, the proximity of a cash register, a book, and a human user can be used to infer the purchase of a book.

Alternatively, baseline profiles can be defined based on values of the data in the data profile. For example, a physical social action can be defined based on a maximum and minimum acceleration, a maximum and minimum force, a maximum and minimum speed, a duration of an acceleration, an orientation of the accelerometer, and other similar features of a data profile. As described above, a given speed, frequency, and waveform can be associated with handshaking. Similarly, other features of a data profile can be associated with walking, running, opening a door, and other physical social actions. Data profiles can also be defined by a user to imply a certain physical action. For example, shaking a book can be defined as borrowing a book from a library.

The comparison engine 224 of the computing device 112 compares a received data profile transmitted from the sensor 104 to a baseline profile (or baseline values) stored in the baseline profile store 220. By comparing the baseline profile to the received data profile, the comparison engine 224 matches the received data profile with a baseline profile, thereby identifying the physical social action.

In another example, the comparison engine 224 checks the timestamp of received data profiles from different but physically proximate sensors (e.g., 104A and 104B) as part of its comparison of the received data profiles. For example, if both sensor 104A and 104B indicate physical proximity to one another, then the comparison engine 224 may compare the timing of movements and the type of physical social action corresponding to the received data profiles. In one embodiment, if two physically proximate sensors transmit data having approximately the same timestamp corresponding to a handshake, the comparison engine 224 may infer that the users of the proximate sensors shook each other's hand.

The communication engine 228 of the computing device 112 receives data transmissions originating at a sensor 104, as described above, and enables other elements of the computing device to access the data profile. The communication engine 228 also communicates the physical social action determined by the comparison engine 224 to the social networking system 116. As described above, the communication engine 228 can receive a unique identifier accompanying a received data profile, where the identifier corresponds to a user of the social networking system 116. The communication engine 228, using this identifier, may access the account of the social networking system 116 user and post the physical social action performed by the user to the social networking system account of the user.

For example, upon the comparison engine 224 determining that the users of sensors 104A and 104B shaken hands, the communication engine 228 receives this analysis from the comparison engine 224, contacts an API of the social networking system 116 and, using the unique identifiers of the users described above in the context of the RFID transceiver 208, posts to the accounts of both of the users that "user A met user B." By making this post, the computing device 112 conveniently and seamlessly extends the open social graph to physical social interactions.

Social Networking System Architecture

Figure 2C:
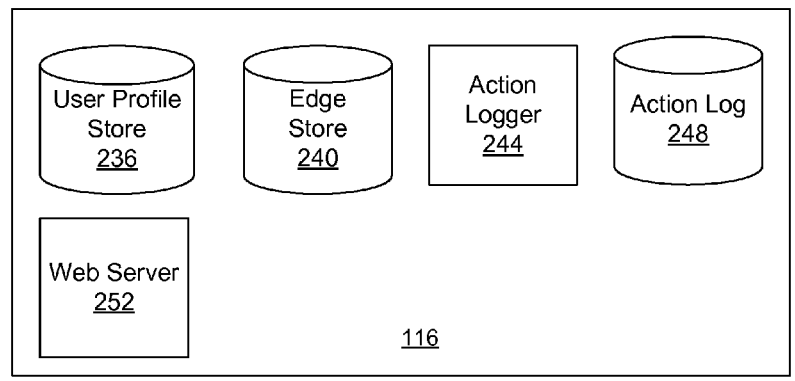
FIG. 2C is a block diagram of a system architecture for a social networking system used to share physical social actions with users of the social networking system, in an embodiment.

FIG. 2C is a block diagram of a system architecture of a social networking system 116 used to receive and publish physical social interactions to an open social graph. The social networking system 116 includes a user profile store 236, an edge store 240, an action logger 244, an action log 248, and a web server 252. In other embodiments, the social networking system 116 may include additional, fewer, or different modules for various applications. Conventional components such as network interfaces, security mechanisms, load balancers, failover servers, management and network operations consoles, and the like are not shown so as to not obscure the details of the system architecture.

Each user of the social networking system 116 is associated with a user profile, which is stored in the user profile store 236. A user profile includes declarative information about the user that was explicitly shared by the user, and may also include profile information inferred by the social networking system 116. In one embodiment, a user profile includes multiple data fields, each data field describing one or more attributes of the corresponding user of the social networking system 116. The user profile information stored in user profile store 236 describes the users of the social networking system 116, including biographic, psychographic, demographic, and other types of descriptive information, such as work experience, educational history, gender, hobbies or preferences, location and the like.

A user profile may also store other information provided by the user, for example, images or videos. In certain embodiments, images of users may be targeted with identification information of the users of social networking system 116 that are displayed in an image. A user profile in the user profile store 236 may also maintain references to actions performed by the corresponding user on social objects in the social networking system 116 and references to physical social actions performed by the user that are stored in the edge store 240.

Because the social networking system 116 receives location and physical social interaction information that users may not wish to share, the user profile store 236 may include one or more privacy settings. These privacy settings may be used to limit the types of information location and/or physical social interaction information that are shared by the social networking system 116. For example, a privacy setting may restrict access to physical social interactions that occur on weekends, during certain hours of the day, and/or during vacations. Alternatively, the privacy settings may be used to restrict the access of other social networking system users to the physical social action information. For example, a privacy setting may restrict designated social networking system users, such as employers, employees, coworkers, and/or family members from viewing some or all of the physical social actions performed by a user. Other similar privacy settings are also possible. Privacy settings may also restrict the type of physical social action that is shared and can restrict whether to share an identity of another user participating in the physical social action. For example, a handshake may be identified within the privacy setting as a physical social action in which the identities of all participants may be shared. But touching a keyboard or exchanging a high-five may be associated with a privacy setting that prohibits sharing the identity of the other participating users.

In one embodiment of the social networking system 116, the edge store 240 stores the information describing connections between users and other objects, including characterized physical social actions, on the social networking system 116 in edge objects. Some edges may be defined by users, allowing users to specify their relationships with other users. For example, users may generate edges with other users that parallel the users' real-life relationships, such as friends, co-workers, partners, and so forth. Other edges are generated when users interact with objects in the social networking system, such as expressing interest in a page on the social networking system 116, sharing a link with other users of the social networking system, and commenting on posts made by other users of the social networking system. Still further edges are generated when a user (or a sensor 104) provides the social networking system 116 with a characterized physical social action. The edge store 240 also stores edge objects that include information about the edge, such as affinity scores for objects, interests, and other users.

The social networking system 116 also includes the action logger 244, which receives information describing user actions on and/or off the social networking system 116, and populates the action log 248 with information about user actions. Actions recorded by the action logger 244 and stored in the action log 248 include those physical social actions identified by the comparison engine 224 of the computing device 112 and shared with the social networking system by the communication engine 228. Other actions stored in the action logger 244 may include, for example, adding a connection to another user, sending a message to another user, uploading an image, reading a message from another user, viewing content associated with another user, attending an event posted by another user, among others.

The action log 248 may be used by the social networking system 116 to track user actions on the social networking system 116, on external websites that communicate information to the social networking system, and outside of the network 108 in physical social actions. Users may interact with various objects on the social networking system 116, including commenting on posts, sharing links, checking-in to physical locations via a mobile device, accessing content items in a sequence, physically interacting with other people or things, or other interactions. Information describing these actions is stored in the action log 248. Additional examples of interactions with objects on the social networking system 116 included in the action log 248 include commenting on a photo album, communications between users, becoming a fan of a musician, adding an event to a calendar, joining a groups, becoming a fan of a brand page, creating an event, authorizing an application, using an application and engaging in a transaction. Additionally, the action log 248 records a user's interactions with advertisements on the social networking system 116 as well as other applications operating on the social networking system. In some embodiments, data from the action log 248 is used to infer interests or preferences of the user, augmenting the interests included in the user profile and allowing a more complete understanding of user preferences.

The web server 252 links the social networking system 116 to devices used by social networking system user to access the system. The web server 252 serves web pages, as well as other web-related content, such as JAVA®, FLASH®, XML and so forth. The web server 252 may provide the functionality of receiving and routing data and messages between a user's social networking system access device and the social networking system 116, using for example, instant messages, queued messages (e.g., email), text and SMS (short message service) messages, or messages sent using any other suitable messaging technique. Additionally, the web server 252 may provide application programming interface (API) functionality to send and receive data directly to native client device operating systems, such as IOS®, ANDROID™, WEBOS® or RIM. The web server 252 also provides API functionality for exchanging data between the computing device 112 and the social networking system 116.

System Interactions

Figure 3:
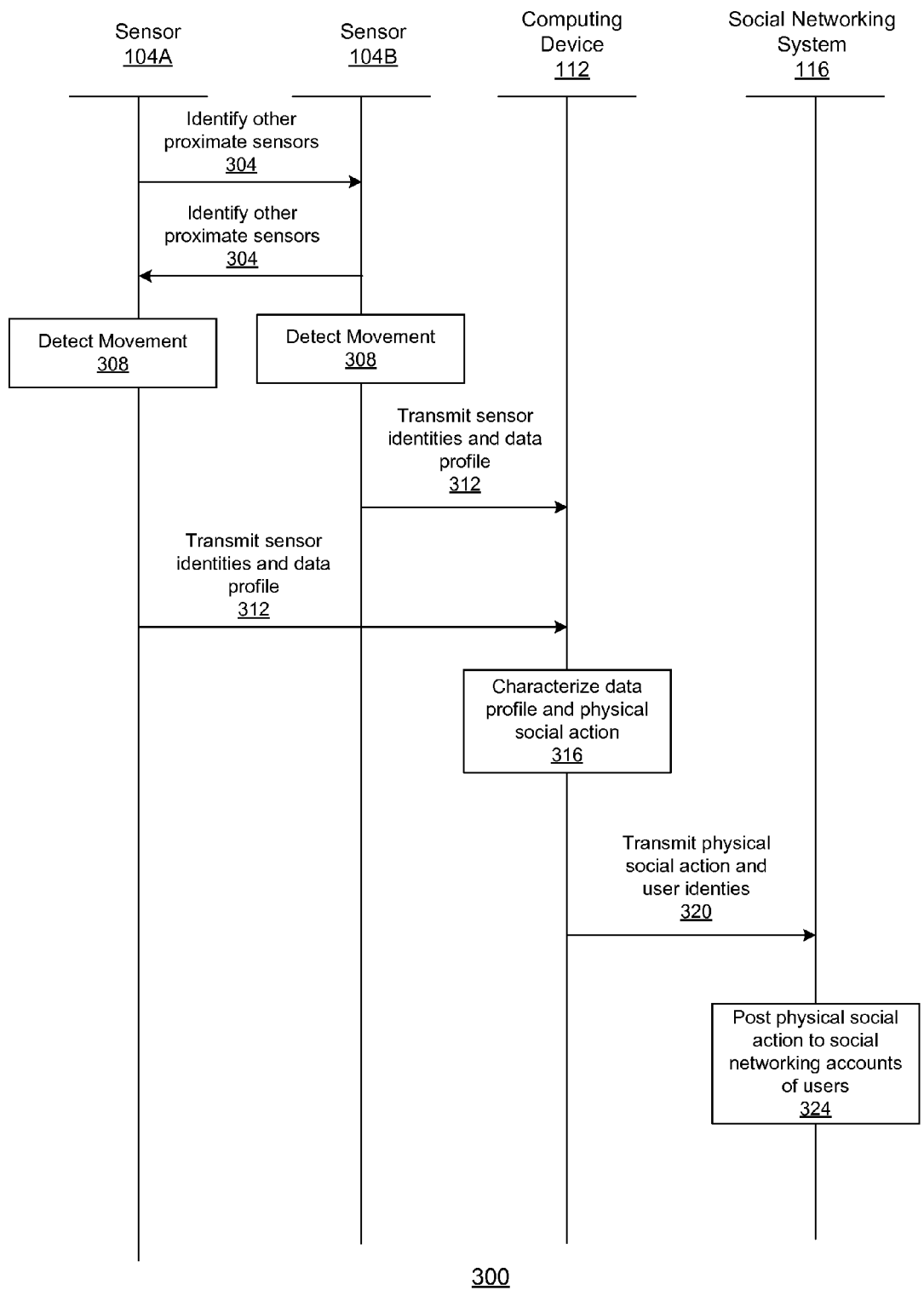
FIG. 3 is an interaction diagram illustrating communications between components of a system environment used for identifying and communicating physical social interactions, in an embodiment.

FIG. 3 illustrates an interaction diagram of a method 300 for detecting, identifying, and communicating physical social interactions to the social networking system 116. In the example shown, the method 300 begins with the sensor 104A identifying 304 the presence of the physically proximate sensor 104B, and vice versa. As described above, this mutual identification of proximately disposed sensors 104 can be used to limit the possible physical social interactions and/or confirm the physical social interactions at and/or between one or more sensors. Furthermore, physically proximate sensors 104A and 104B not only detect each other, but also other proximate sensors within the range of their respective RFID transceivers, whether or not the other sensors are participating in the physical social action.

Upon identifying 304 the proximate sensors 104, the sensors 104A and 104B use their respective accelerometers 204 to detect 308 movements of the sensors. Having thus identified 304 proximate sensors and detected movement 308 of at least one sensor 104, the sensors 104A and 104B then transmit 312 the proximate sensor identities and data profiles of the movement to the computing device 112.

Upon receipt of the transmitted 312 data profiles and sensor identities 312, the computing device 112 characterizes 316 the data profile as a physical social action. As described above, characterizing 316 the data profile can include reference to a baseline profile and/or specific values in the data profile. These values include, but are not limited to, acceleration value, acceleration direction, frequency, orientation, and location. As explained above, the baseline profile and/or specific values can be generic to some or all users of the system 100 or alternatively can be associated with specific users.

Once the computing device 112 characterizes 316 the data profile (or profiles) as a physical social action, the characterization is transmitted 320 to the social networking system. Because the characterized physical social action is most meaningful when associated with specific users of the social networking system 116, the computing device 112 transmits identities of the sensors 104 such that the physical social action can be posted to one or more accounts of social networking users. This can include transmitting the RFID unique identifier of the sensor 104 that is used by the social networking system 116 to specifically identify the social networking system user associated with the RFID identifier. This correlation between the RFID unique identifier and social networking system 116 user profile can also be performed at the computing device 112. In this later case, the data profile, the user social networking system identity, and security credentials are all transmitted to the social networking system 116 using, for example, the API functionality of the web server 252. Regardless of how the characterized social action is transmitted 320 to the social networking system 116 and associated with a user of the social networking system, the system posts 324 the physical social interaction to the accounts of the users associated with the physical social action. Upon posting the physical social action, the open social graph has been extended to physical social interactions.

One specific example of this interaction is between a human user and a book, both of which bear a sensor 104. In this example, the sensor 104A associated with the human user and the sensor 104B associated with the book identify 304 each other as being proximate. Upon the human user picking up the book from stationary position, both sensors 104A and 104B detect 308 the movement, and transmit 312 the data profile and sensor identities to the computing device 112 for analysis. The computing device 112 then characterizes 316 the data profile according to any one or more of stored baseline profiles. In this example, embodiments of baseline profiles include, but are not limited to checking out the book from a library (e.g., by shaking it or some other defined baseline profile associated with checking out the book), turning a page of the book, handing the book to another, and/or replacing the book on a shelf. Once characterized 316, the physical social action is transmitted 320 to a social networking system 116 along with the identities of the sensors 104A and 104B, which correspond to identities on the social networking system.

The social networking system 116, upon receiving the transmitted social actions and user identities posts 324 the physical social action to the appropriate user accounts. In this example, if the human user 104 begins turning pages at regular intervals, the social networking system 116 can create an open graph story with an initial post stating "User A is reading Book B." Because the system 100 can determine how long the sensor 104A has been stationary and approximately how many pages have been turned (and/or read) at a sitting, the social networking system 116 can add to the story by identifying further physical social interactions between the user and the book. For example, the social networking system can post an additional physical social action to the open graph story stating "User A loves Book B" if the user has remained stationary for a period of more than one hour and turned more than 50 pages. The social networking system 116 can also connect a user reading a particular book with other users reading the same book (or books by the same author, in the same genre, etc.) because the book is uniquely identified by the sensor 104B. These connections can then also be posted to a user account.

In another example, a human user using the sensor 104A can enter a café that has attached sensor 104B to its door. Following an analogous interaction between the sensors 104A and 104B, an open graph story can be started (on one or both social networking system accounts of the human user and the café) that the user has entered the café. Further additions to the open graph story can be added depending on who the user of sensor 104A meets within the café, what objects the user interacts with, and how long the user remains.

Other Applications

While the above embodiments are focused primarily on extending the open social graph to physical social interactions, the system 100 can be used for other applications. In some applications, the system 100 can be used to provide information from the social networking system 116 to the sensor 104. For example, information can be sent to the sensor 104 from the social networking system to indicate other proximate social networking system users. In one example, upon the sensor 104A communicating the unique RFID identities of other proximate sensors (e.g. 104B) to the social networking system 116, the social networking system can then transmit to the sensor 104A the social networking system identities of the proximate users. Furthermore, the social networking system 116 can search the edge store 240 associated with the user of the sensor 104A to provide the user of the sensor 104A with information regarding other social networking system users to whom the user of sensor 104A is connected.

In the foregoing example, this information can be displayed on a properly configured sensor 104 (e.g., a sensor that includes a display) or be displayed on a mobile computing device in communication with one or both of the sensor and the social networking system 116. In one embodiment, because the sensor 104 includes both an RFID transceiver 208 and a network transceiver 212, the sensor can communicate to a mobile computing device that is similarly enabled for wireless communication and properly paired with the sensor. In this way, information sent by the social networking system 116 to the sensor 104 can be displayed on the mobile computing device using, for example, a social networking system 116 mobile application or Internet browser.

In another application, because the sensor 104 includes a unique RFID identifier that is associated with a user's social networking system 116 account, the sensor can be used to log a user into the social networking system in lieu of user-submitted security credentials (such as a username and password). Using the unique RFID identifier of the sensor 104 in lieu of security credentials is not merely limited to social networking systems 116. Rather, because the sensor 104 can communicate through the network transceiver 212 to any device or system connectable to the network 108, the sensor can be used in lieu of security credentials for any system in communication with the network. The benefit of using the sensor 104 in lieu of user-submitted security credentials is that a user can passively use the sensor to access any of a number of applications and resources rather than attempting to remember a plurality of different login credentials. Furthermore, the unique identifier stored by the RFID transceiver 208 can provide greater security than some login credentials that are susceptible to discovery.

Furthermore, the unique RFID identifier can be used to access user-specific settings that can personalize a computing device or an apparatus that includes a computing device. For example, a user using a properly configured sensor 104 can use the sensor to access a user account that provides a computing device with the user's selected settings. In an embodiment of this example, a sensor 104 can be used to access a cloud-computing based e-reader platform, which then transmits user-specific e-reader account information to the e-reader. This personalizes any e-reader according to account identity corresponding to the sensor 104. Other similar applications used to personalize a computing device are possible.

In an alternative embodiment, a user can enter a space equipped with a sensor 104 that identifies the user by using the unique RFID identifier associated with the user's sensor. Music systems connected to the sensor 104 of the space can then list the user as a collaborator or contributor to a social music service queuing music to be played in the space, thereby adding one or more songs associated with the individual user's social music service account.

The system 100 can also be used to track the "virality" of a particular preference, song, association, a social object or physical social action. This can be done by monitoring interactions between users participating in the system 100 by using sensor 104 and, for example, the first exposure or access by a user to the particular preference, song, etc. In other words, the progression of a preference through a networking of connected users can be mapped as a function of time. This can also be used as a way of identifying individual users that expose a disproportionate number of other users to the preference.

In yet another application, the sensor 104 can be used in specific settings in which identifying physical social actions is helpful, beyond the more general examples of attending a conference or party described above. For example, the sensor 104 can be used as a helpful tool in live action role playing ("LARP"). The sensor 104 can be used to automatically detect interactions integral to a game. In one embodiment of the LARP game "Humans vs. Zombies," the apparatus and systems described above can be used to detect that user A, playing a human, was chased by user B, playing a zombie, and ultimately tagged by user B. The benefit of this feature is that interactions that are critical to the performance of the game can be recorded automatically (and optionally posted to the social networking system 116) without interrupting the flow of the game.

Continuing with this example, the sensor 104 can also be used to provide user-specific instructions during LARP, such as the duration of time-outs, the duration that a user is required to play a particular role, and other similar rules and/or instructions. The benefit of this application is that the game can be performed seamlessly with the assistance of the sensor 104, unlike traditional LARP which often requires the players to interrupt the flow of the game to consult rules, timers, record interactions, and the like. Furthermore, to facilitate this application (and other embodiments described above), the sensor 104 may be optionally configured to include a visual or tactile indicator, such as an LED or haptic feedback, to indicate the performance of a physical social action. Similarly, the sensor 104 can also be integrated into more traditional games, such as football, basketball, and others.

In another application, the sensors 104 are not necessarily used with a social networking system 116, but instead are used primarily as indicators used to infer an action from other systems. For example, if the sensor 104A is associated with a human user and the sensor 104B is associated with a blanket, proximity and movement of the two sensors can be used by the system 100 to trigger a heating system in a dwelling of the human user. Similarly, the sensor 104 can be used to automatically turn household lights on and off, open automatic doors, and the like. The sensor 104 can also interact with home automation systems to turn appliances on and off, control home entertainment systems, change lighting levels, and the like.

In still another application, the system 100 can be used to monitor interactions between users (whether human, non-human, or inanimate) in a controlled setting, such as a conference or employer-sponsored retreat. For example, the number of people at a conference location can be monitored, the locations of the people within the conference center, and the interactions between the conference attendees. Furthermore, using the user profiles from social networking system 116 accounts associated with the conference attendees, patterns in interactions between attendees can be identified. These patterns can include common interests, hobbies, group associations, musical preferences, and the like. Other interactions such as menu and drink preferences (in the case of food or beverage containers or serviceware fitted with a (typically passive) RFID chip identifying the food or beverage being served), attendance at particular sessions of the conference, and popular meeting locations within a conference center can also be identified. These interactions can be of particular use to the conference organizers in anticipating the needs of their clients.

Additional Considerations

The foregoing description of the embodiments has been presented for the purpose of illustration; it is not intended to be exhaustive or to limit the embodiments to the precise forms disclosed. Persons skilled in the relevant art may appreciate that many modifications and variations are possible in light of the above disclosure.

Some portions of this description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which may be executed by a computer processor for performing any or all of the steps, operations, or processes described.

Embodiments may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the embodiments be limited not by this detailed description, but rather by any claims that issue on an application based hereon. Accordingly, the disclosure of the embodiments is intended to be illustrative, but not limiting, of the scope of the embodiments, which is set forth in the following claims.

What is claimed is:

1. A method comprising:
    storing, by a social networking system, a social graph comprising a plurality of nodes and edges, wherein a node represents a user or an entity and an edge represents one of a connection between users or an interaction between users performed via the social networking system;
storing a plurality of baseline data profiles representing physical social interactions associated with users, wherein the baseline data profiles are created based at least in part on using a machine learning technique and a baseline data profile specifies a physical movement of a sensor;
receiving, from a first sensor associated with a first user, a data profile characterizing an interaction between the first sensor and a second sensor associated with a second user as a function of a physical movement of the first sensor;
receiving a user identifier corresponding to the first user and the data profile characterizing the interaction;
comparing the received data profile characterizing the interaction to the plurality of baseline data profiles to identify a matching baseline data profile responsive to a matching of the physical movement specified by the data profile with the physical movement specified by the matching baseline data profile;
identifying a physical social interaction associated with the first user and the second user based on the matching baseline data profile;
adding a new edge to the social graph of the social networking system, the new edge representing the identified physical social interaction; and
notifying one or more other users of the social networking system that the first user engaged in the physical social interaction with the second user.

2. The method of claim 1, further comprising receiving a profile of a proximate, contemporaneously detected physical movement by the second user and a user identifier of the second user.

3. The method of claim 2, further comprising determining that the first user and the second user have engaged in a joint physical social interaction based on the proximate, contemporaneously detected physical movement.

4. The method of claim 1, wherein the baseline data profile corresponds to a profile generated by the first user and associated by the first user with a corresponding physical social interaction.

5. The method of claim 1, wherein the baseline data profile corresponds to a plurality of profiles identified as corresponding to a physical social interaction by a plurality of users of the social networking system.

6. The method of claim 1, wherein identifying the physical social interaction includes identifying a movement profile and the user identifier as a security credential.

7. The method of claim 1, wherein the second user is one of: a human user or an inanimate object.

8. The method of claim 1, wherein the second sensor is associated with the second user that is a book and the identified physical social interaction represents an interaction performed by the first user with the book.

9. The method of claim 1, wherein the second sensor is associated with the second user that is a door and the identified physical social interaction represents the first user opening the door.

10. The method of claim 1, wherein the identified physical social interaction represents the first user shaking hands with the second user.

11. The method of claim 1, further comprising:
extending a social graph representation of the social networking system to include physical social actions by recording the identified physical interation in the social graph.

12. A method comprising:
storing, by a social networking system, a social graph comprising a plurality of nodes and edges, wherein a node represents a user or an entity and an edge represents one of a connection between users or an interaction between users performed via the social networking system;
storing a plurality of baseline data profiles representing physical social interactions associated with users, wherein a baseline data profile specifies a physical movement of a sensor;
receiving at least two data profiles of contemporaneously detected physical movements corresponding to at least two proximately disposed users of a social networking system, the two data profiles comprising a first data profile received from a first sensor and a second data profile received from a second sensor, the two data profiles characterizing a physical social interaction as a function of physical movements of the first and second sensors;
receiving a user identifier corresponding to each of the at least two proximately disposed users of the social networking system;
comparing the received data profiles characterizing the physical social interaction to the plurality of baseline data profiles to identify a matching baseline data profile responsive to a matching of the physical movements specified by the data profiles with the physical movement profiles specified by the matching baseline data profile;
identifying the physical movement profiles as corresponding to the physical social interaction between the two proximately disposed users based on the matching baseline data profile;
adding a new edge to the social graph of the social networking system, the new edge representing the identified physical social interaction; and
communicating the physical social interaction to one or more other users of the social networking system.

13. The method of claim 12, wherein identifying the physical movement profiles as corresponding to a physical social action comprises matching each of the profiles to at least one baseline profile of a physical social interaction.

14. The method of claim 13, wherein the baseline profile corresponds to a profile generated by the user and associated by the user with a corresponding physical social interaction.

15. The method of claim 13, wherein the baseline profile corresponds to a plurality of profiles identified as corresponding to a physical social interaction by a plurality of users of the social networking system.

16. The method of claim 13 wherein one of the proximately disposed users is inanimate.

17. A system comprising:
a sensor comprising:
a movement sensor associated with a first user for detecting a physical movement of the movement sensor with a proximate sensor associated with another user;
a processor in communication with the movement sensor, the processor for generating a physical movement profile comprising a data profile characterizing the detected interaction as a function of the physical movement;

a local area identity transceiver for transmitting and receiving at least one user identifier; and a network transceiver for communicating at least one of the physical movement profile and the user identifier; and a computing device in communication with the sensor, the computing device for:

storing a social graph comprising a plurality of nodes and edges, wherein a node represents a user or an entity and an edge represents one of a connection between users or an interaction between users performed via the social networking system;

storing a plurality of baseline data profiles representing physical social interactions associated with users, wherein a baseline data profile specifies a physical movement of a sensor;

receiving the physical movement profile from the sensor, the physical movement profile comprising the data profile characterizing an interaction between the sensor and the proximate sensor;

comparing the received physical movement profile to the plurality of baseline data profiles to identify a matching baseline data profile responsive to a matching of the physical movement specified by the data profile with the physical movement specified by the matching baseline data profile;

identifying a physical social interaction corresponding to the physical movement profile based on the matching baseline data profile;

adding a new edge to the social graph of the social networking system, the new edge representing the identified physical social interaction; and notifying one or more other users of the social networking system that the first user engaged in the physical social interaction with the other user.

18. The system of claim 17, wherein the local area identity transceiver is for detecting a user identifier corresponding to the proximate sensor associated with the other user.

19. The system of claim 18, wherein the physical social interaction further is associated with the proximate sensor of the other user.

20. The system of claim 18, wherein the other user is an establishment.

21. The system of claim 17, wherein the account of the social networking system is associated with the sensor by executing a recognized pairing movement.

22. The system of claim 17, wherein the sensor further comprises an image capture system.

23. A non-transitory computer-readable medium that includes instructions that, when loaded into memory, cause a processor to perform a method, the method comprising:

storing, by a social networking system, a social graph comprising a plurality of nodes and edges, wherein a node represents a user or an entity and an edge represents one of a connection between users or an interaction between users performed via the social networking system;

storing a plurality of baseline data profiles representing physical social interactions associated with users, wherein a baseline data profile specifies a physical movement of a sensor;

receiving, from a first sensor associated with a first user, a data profile characterizing an interaction between the first sensor and a second sensor associated with a second user as a function of a physical movement of the first sensor;

receiving a user identifier corresponding to the first user and the data profile characterizing the interaction;

comparing the received data profile characterizing the interaction to the plurality of baseline data profiles to identify a matching baseline data profile responsive to a matching of the physical movement specified by the data profile with the physical movement specified by the matching baseline data profile;

identifying a physical social interaction associated with the first user and the second user based on the matching baseline data profile;

adding a new edge to the social graph of the social networking system, the new edge representing the identified physical social interaction; and notifying one or more other users of the social networking system that the first user engaged in the physical social interaction with the second user.

24. The computer-readable medium of claim 23, further comprising receiving a profile of a proximate, contemporaneously detected physical movement by the second user and a user identifier of the second user.

25. The computer-readable medium of claim 24, further comprising determining that the user and the proximate user have engaged in a joint physical social interaction based on the detected physical movement and the proximate, contemporaneously detected physical movement.

26. The computer-readable medium of claim 23, wherein the baseline data profile corresponds to a profile generated by the user and associated by the user with a corresponding physical social interaction.

27. The computer-readable medium of claim 23, wherein the baseline data profile corresponds to a plurality of data profiles identified as corresponding to a physical social interaction by a plurality of users of the social networking system.

28. The computer-readable medium of claim 23, wherein identifying a physical social interaction includes identifying a movement profile and the user identifier as a security credential.

* * * * *